United States Statutory Invention Registration [19]

[11] Reg. Number: H443

Sommer et al. [43] Published: Mar. 1, 1988

[54] CHEMICAL AGENTS

[75] Inventors: Harold Z. Sommer, Havre de Grace; Omer O. Owens, Abingdon, both of Md.

[73] Assignee: The United States of America as represented by the Secretary of the Army, Washington, D.C.

[21] Appl. No.: 645,564

[22] Filed: Jun. 7, 1967

[51] Int. Cl.[4] ..... C07C 125/04; A61K 31/27

[52] U.S. Cl. ..... 560/133

[58] Field of Search ..... 260/482 C; 167/46 A, 167/47; 424/300; 560/133; 514/483

[56] References Cited

U.S. PATENT DOCUMENTS 3,188,955 6/1965 Brown ..... 102/24

FOREIGN PATENT DOCUMENTS 782789 9/1957 United Kingdom ..... 260/482

*Primary Examiner*—John F. Terapane
*Assistant Examiner*—J. E. Thomas
*Attorney, Agent, or Firm*—Anthony T. Lane; Harold H. Card, Jr.; Edward F. Costigan

[57] ABSTRACT

New chmeical compounds having the generic formula:

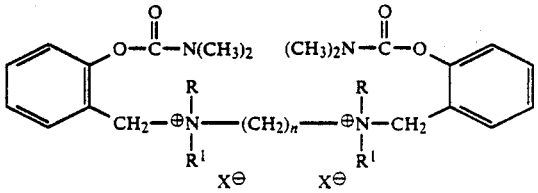

wherein n is 5–16, R, R′ are radicals selected from the group consisting of methyl, ethyl, propyl, isopropyl, butyl, and X is one equivalent of an anion selected from the group consisting of monovalent or polyvalent anions, and having utility as toxic agents and in munitions.

3 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

CHEMICAL AGENTS

This invention relates to the synthesis of new toxic chemical compounds which are useful as chemical warfare agents. More particularly, our invention is concerned with novel compounds produced by means of a quaternizing reaction.

The chemical agents act mostly on the peripheral cholinergic nervous system which includes the motor nerves, the preganglionic fibers, the ganglia, the postganglionic parasympathetic fibers, and neuromuscular functions. The transmission of impulses along a nerve or from nerve fibers to muscle fibers or secretory cells or from one nerve fiber to another across synapses in ganglia is thought to involve chemical changes either directly or as the source of potential differences.

Quaternary ammonium compounds in general are known to be physiologically active materials. Mainly because of their positively charged "onium" centers they are attracted by anionic sites in animal tissues, particularly those situated at cell surfaces and interfaces. They can induce physiological responses that mimic or antagonize the action of acetylcholine as a result of their interaction with the various physiological receptor sites of acetylcholine, especially those at membranes of muscle cells. They also combine with enzymes such as acetylcholinesterase, other esterases, acetylcholineacetylase, etc., thus inhibiting their participation in the biological processes.

One of the significant anatomical differences between the neuromuscular junctions and other acetylcholine receptive sites is the absence of a membrane barrier or a sheath such as envelops the ganglia. The comparative ease of accessibility of the neuromuscular junctions to "onium" compounds contributes to their relatively fast onset of action and partly explains why in many instances relatively small doses suffice to evoke physiological actions that modify or interrupt normal neuromuscular impulse transmission.

Depending on their chemical structures different quaternary compounds interfere with the mechanism of impulse transmission in different manners and the final physiological effects can vary considerably. Some quaternary ammonium compounds are used as therapeutic agents, others are known to be lethal. The magnitude, accessibility, and distribution of the positive charges in quaternary compounds are believed to be the key factors in the determination of specificity of action. Recognition of these facts explains the strikingly different physiological behavior so often observed when structurally very closely related compounds are compared. The nature of the groups attached to the quaternary nitrogens influences the distribution of the cationic charges. The length and branching of aliphatic chains and the volume and configuration of aromatic and alicyclic rings have a bearing on the ease or difficulty of approach to the specific receptor sites. Electrophilic and nucleophilic centers in the molecule will insert their inductive effects on the positive charges and can also aid in the interaction with the "esteratic sites" of various enzymes. These sites are believed to be located in close vicinity to the anionic sites of the active centers. Substitution of different functional groups, which influence association and hydration, may considerably change the solubilities in physiological media. In bisquaternary and poly-quaternary compounds, the distance between the electric charges must be considered.

These factors contribute to govern the rate and reversibility of the chemical reactions involved, and contribute to determine the final physiological responses.

Our chemical agents interfere with the normal process of neuromuscular impulse transmission and thus disrupt the propagation of impulses from nerves to muscles. We have also found these compounds to be extremely toxic at relatively low dose levels in various animals.

The object of this invention is to synthesize new lethal agents useful in chemical warfare in high yields wherein said products are well suited for industrial scale manufacture.

Our compounds may be employed in any munition suitable for handling a relatively non-volatile toxic agent such as bombs, shells, spray tanks, rockets, missiles, aerosol generators, and others.

Other objects of and uses for the invention will in part be obvious and will in part appear hereinafter in the following detailed description thereof.

In accordance with our invention an aminocarbamate, such as (2-dimethylcarbamoxybenzyl)methylethylamine, and an $\alpha,\omega$-dihaloalkane such as 1,8-dibromooctane, were dissolved in a solvent such as acetonitrile and refluxed for 2–6 days. The solution was concentrated and upon addition of a solvent such as ethyl acetate, an oily material separated. After stirring the oil in acetone for a few minutes, the acetone was decanted. The residue was dissolved in a solvent such as acetonitrile, the solution treated with decolorizing charcoal, and a solvent such as ethyl acetate was added. A white solid material formed that was separated by filtration and dried. The white crystalline material thus obtained constitutes new compounds of the present invention which may be represented by the following generic formula:

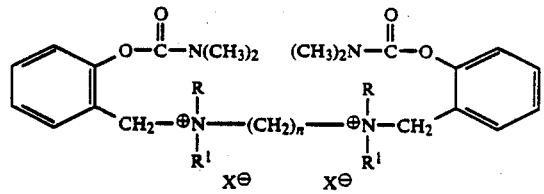

wherein n is 5–16, R, R' are radicals selected from the group consisting of methyl, ethyl, propyl, isopropyl, and butyl, and where X is one equivalent of an anion selected from the group consisting of monovalent or polyvalent anions.

The procedure used for the preparation of the new toxic materials is schematically shown below:

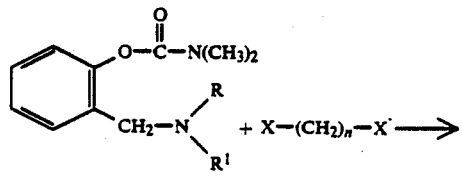

-continued

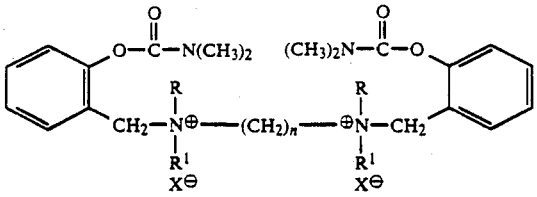

wherein X is a halide and n and R, R' as defined above.

If compounds are desired in which X is other than a halide ion, the above quaternary compounds are treated with the desired acid by simple exchange reaction as set forth below.

The aminocarbamates were prepared by the Mannich Reaction on phenol with the desired secondary amines and subsequent carbamoylation of the resultant Mannich bases with dimethylcarbamoyl chloride, schematically shown below:

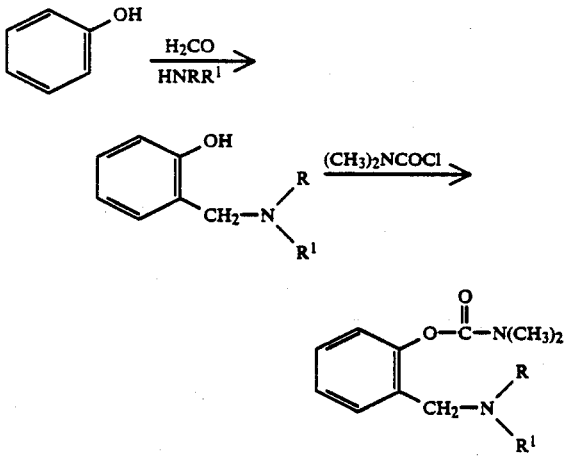

wherein R and R' are radicals selected from the group consisting of methyl, ethyl, propyl, isopropyl, and butyl.

EXAMPLE 1

(2-Dimethylcarbamoxybenzyl)methylethylamine (1.4 g) and 1,8-dibromooctane (0.8 g) were dissolved in 10 ml of acetonitrile and refluxed on a steam bath for 3 days. After the solution was allowed to cool to room temperature, ethyl acetate (30 ml) was added and an oil separated from the solution. The oil solidified upon stirring in acetone. The crude product thus obtained was collected on a filter and purified by dissolving it in acetonitrile, treating the solution with decolorizing carbon, and adding ethyl acetate. The white crystalline product, 1,8-bis[(2-dimethylcarbamoxybenzyl)ethylamino]octane dimethobromide (0.5 g) was collected and dried, m.p. 176°-178° C.

Anal. Calcd. for $C_{34}H_{56}Br_2N_4O_4$: Calcd: C, 54.8; H, 7.5; Br, 21.5. Found: C, 55.0; H, 7.9; Br, 21.2.

| Toxicity IV $LD_{50}$ | |
|---|---|
| Rabbits | Mice |
| 0.005 mg/kg | 0.007 mg/kg |

EXAMPLE 2

The reactants, (2-dimethylcarbamoxybenzyl)methylpropylamine (2.0 g) and 1,10-dibromodecane (1.2 g) were dissolved in 10 ml of acetonitrile and refluxed on a steam bath for 4 days. After the solution was allowed to cool to room temperature, ethyl acetate was added and an oil separated out of solution. The solvent was decanted and the remaining oil was stirred in acetone. The acetone was decanted and the gummy residue was dissolved in acetonitrile, treated with decolorizing carbon, and to the solution ethyl acetate added. The viscous oil that precipitated was collected and dried under vacuum (0.2 mm) over phosphorous pentoxide. 1.4 g of white crystalline product, 1,10-bis[(2-dimethylcarbamoxybenzyl) propylamino]decane dimethobromide, m.p. 82°-84° C., was obtained.

Anal. Calcd for $C_{38}H_{64}Br_2N_4O_4.1H_2O$: Calcd: C, 55.7; H, 8.1; Br, 19.6; O, 9.8. Found: C, 55.8; H, 8.2; Br, 19.7; O, 9.4.

| Toxicity IV $LD_{50}$ | |
|---|---|
| Rabbits | Mice |
| 0.010 mg/kg | 0.045 mg/kg |

The compounds that are representative of our invention are listed below by name and chemical structure:

1,6-Bis[(2-dimethylcarbamoxybenzyl)ethylamino]hexane dimethobromide.

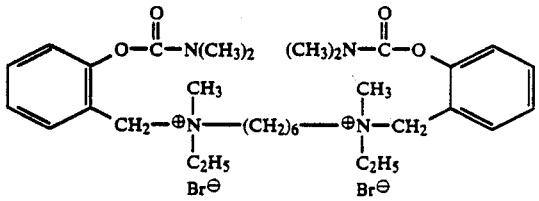

1,7-Bis[(2-dimethylcarbamoxybenzyl)ethylamino]heptane dimethobromide.

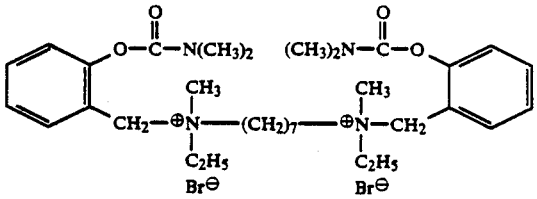

1,8-Bis[(2-dimethylcarbamoxybenzyl)ethylamino]octane dimethobromide.

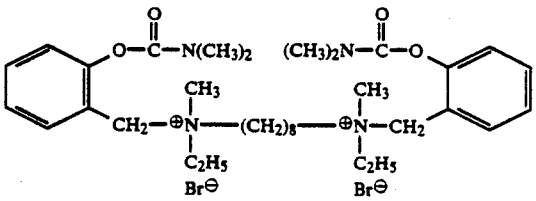

1,10-Bis[(2-dimethylcarbamoxybenzyl)ethylamino]decane dimethobromide.

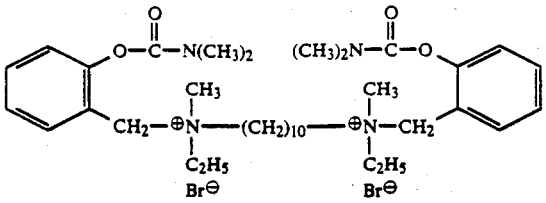

1,16-Bis[(2-dimethylcarbamoxybenzyl)ethylamino]hexadecane dimethobromide.

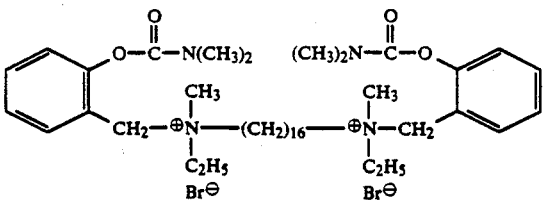

1,8-Bis[(2-dimethylcarbamoxybenzyl)ethylamino]octane diethobromide.

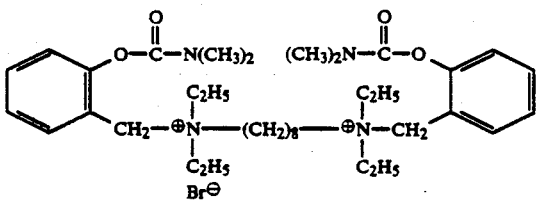

1,10-Bis[(2-dimethylcarbamoxybenzyl)propylamino]-decane dimethobromide.

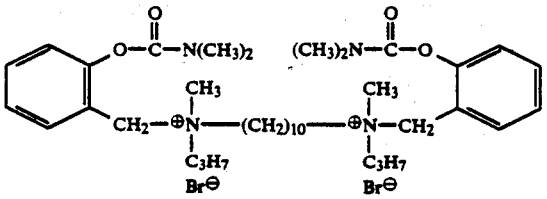

1,10-Bis[(2-dimethylcarbamoxybenzyl)isopropylamino]decane dimethobromide.

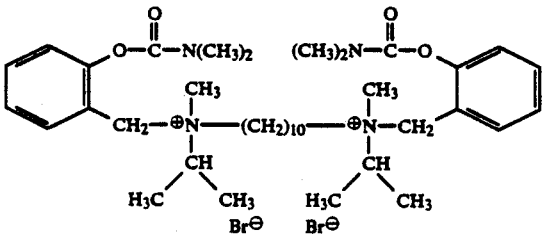

1,10-Bis[(2-dimethylcarbamoxybenzyl)butylamino]decane dimethobromide.

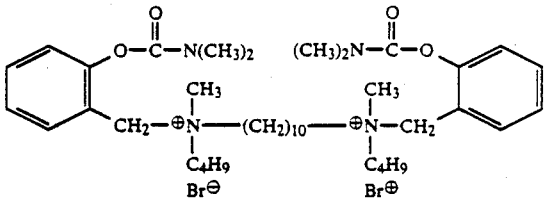

We have shown preferred compounds in which the anion is limited to a halogen, in particular the bromide, since the dibromoalkanes are readily available and are good quaternizing agents. In general, however, it is only necessary that the anions merely have to meet the requirement of being capable of forming a stable salt with the quaternary nitrogens. Thus, the halogen ion can be exchanged with other anions of a relatively strong monovalent or polyvalent acid by conventional methods. For example, if X is a bromide in the quaternary compound, it can be treated with a basic ion exchange resin or mixed with silver oxide and subsequently the desired acid is added. In like manner the hydrogen oxalate, nitrate, perchlorate, and hydrogen sulfate may be prepared.

Representative examples of these additional quaternary salts are:

1,8-Bis[(2-dimethylcarbamoxybenzyl)ethylamino]octane di(hydrogen methoxalate).

1,8-Bis[(2-dimethylcarbamoxybenzyl)ethylamino]octane dimethonitrate.

1,8-Bis[(2-dimethylcarbamoxybenzyl)ethylamino]octane di(hydrogen methosulfate).

1,8-Bis[(2-dimethylcarbamoxybenzyl)ethylamino]octane dimethoperchlorate.

We claim:

1. Chemical compounds having the generic formula:

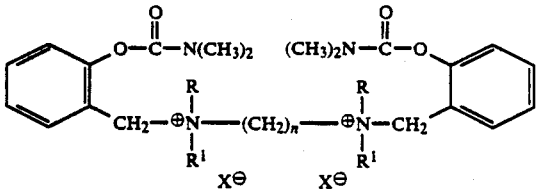

wherein n is selected from 5–16; R, R′ are radicals selected from the group consisting of methyl, ethyl, propyl, isopropyl, and butyl; and X is one equivalent of an anion selected from the group consisting of monovalent and polyvalent anions, said anions being selected from the group consisting of halide, hydrogen oxalate, perchlorate, hydrogen sulfate, and nitrate.

2. Chemical compounds selected from the group of compounds having the names:

1,8-bis[(2-dimethylcarbamoxybenzyl)ethylamino]octane dimethobromide;

1,10-bis[(2-dimethylcarbamoxybenzyl)ethylamino]decane dimethobromide;

1,10-bis[(2-dimethylcarbamoxybenzyl)ethylamino]decane diethobromide;

1,10-bis[(2-dimethylcarbamoxybenzyl)propylamino]-decane dimethobromide; and 1,10-bis[(2-dimethylcarbamoxybenzyl)butylamino]decane dimethobromide.

3. A method of producing a chemical compound having the generic formula:

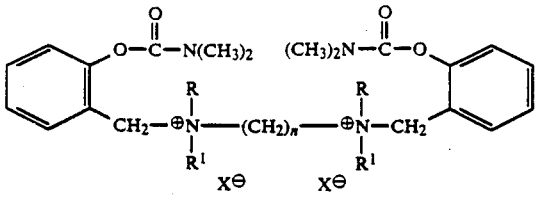

wherein n is selected from 5–16; R, R′ are radicals selected from the group consisting of methyl, ethyl, propyl, isopropyl, and butyl; and X is a halide comprising the steps of dissolving a (2-dimethylcarbamoxbenzyl) R amine wherein R is selected from the group consisting of methyl, ethyl, propyl, isopropyl, and butyl, and an α, ω-dihaloalkane selected from the group consisting of 1,8-dihalooctane and 1,10-dihalodecane in a solvent; refluxing the amine-dihaloalkane solution, cooling the refluxed solution; adding ethyl acetate to the cooled solution to separate an oil out of solution; decanting the solvent from the amine-dihaloalkane—ethyl acetate solution to leave the oil; stirring the oil in acetone; decanting the acetone to leave a gummy residue; dissolving the gummy residue in acetonitrile; treating the gummy residue acetonitrile solution with decolorizing carbon; adding ethyl acetate to the gummy residue—acetonitrile decolorizing carbon solution to precipitate a viscous oil; drying the viscous oil.

* * * * *